United States Patent
Drivon et al.

(10) Patent No.: US 6,906,219 B2
(45) Date of Patent: Jun. 14, 2005

(54) METHOD FOR PREPARING BROMODIFLUOROACETIC COMPOUNDS

(75) Inventors: Gilles Drivon, Saint-Martin-en-Haut (FR); Jean-Philippe Gillet, Brignais (FR); Christophe Ruppin, Pierre-Benite (FR)

(73) Assignee: Atofina, Puteaux (FR)

( * ) Notice: Subject to any disclaimer, the term of this patent is extended or adjusted under 35 U.S.C. 154(b) by 216 days.

(21) Appl. No.: 10/173,567

(22) Filed: Jun. 18, 2002

(65) Prior Publication Data

US 2003/0032836 A1 Feb. 13, 2003

(30) Foreign Application Priority Data

Jun. 18, 2001 (FR) .............................................. 01 07943

(51) Int. Cl.$^7$ ......................... C07C 69/63; C07C 51/00
(52) U.S. Cl. ....................................... 560/227; 562/604
(58) Field of Search .......................... 560/227; 562/604, 562/605

(56) References Cited

U.S. PATENT DOCUMENTS 4,340,548 A  7/1982  Anello et al.

FOREIGN PATENT DOCUMENTS

DE          1020970       12/1957

OTHER PUBLICATIONS

General Chemical Corporation, Technical Service Report No. 52.79, Recommendendations for the Storage and Handling of 15% to 25% and 65% Commerical Oleum, 1997, Delaware.*

Abstract of JP 11080084 along with an English translation of entire article.

G.A. Grindahl et al.; "The Preparation and Coupling of Some Alpha–Haloperfluoromethyl–s–triazines"—Journal of Organic Chemistry., vol. 32, 1967, pp. 603–607, XP002192250, American Chemical Society, Easton., U.S. ISSN: 0022–3263.

Morel et al.: "Synthese d'un nouveau monomere hydrofluorocarboxylique: Le difluoro–2,2–butene–3–oate d'ethyle" Tetrahedron., vol. 33, 1977, pp. 1445–1447, XP002192251, Elsevier Science Publishers, Amsterdam, NL, ISSN: 0040–4020.

* cited by examiner

*Primary Examiner*—Johann Richter
*Assistant Examiner*—Paul A. Zucker
(74) *Attorney, Agent, or Firm*—Millen, White, Zelano & Branigan, P.C.

(57) ABSTRACT

The invention relates to a method for preparing bromodifluoroacetic compounds which comprises converting a 1,1-difluoro-1,2-dibromodihaloethane with oleum having 50–70% $SO_3$ to a bromodifluoroacetyl halide (bromide or chloride) and then in reacting the latter directly with either an alcohol, or with water.

18 Claims, No Drawings

METHOD FOR PREPARING BROMODIFLUOROACETIC COMPOUNDS

The present invention relates to a method for preparing bromodifluoroacetic compounds such as bromodifluoroacetic acid or its esters and alkyl bromodifluoroacetates.

Bromodifluoroacetic compounds are intermediates in the synthesis of pharmaceutical and plant-protection products.

Numerous methods have been described for obtaining these compounds, which methods most often involve reacting an alcohol with a bromodifluoroacetyl halide for the production of bromodifluoroacetic acid esters, the latter being obtained by hydrolysis of the said halides.

These bromodifluoroacetyl halides (fluoride, chloride or bromide) may be obtained according to a wide variety of techniques.

In the Journal of Organic Chemistry, 33 (2) p. 816–9 (1968) a method is described for obtaining bromodifluoroacetyl chloride which comprises the following steps:

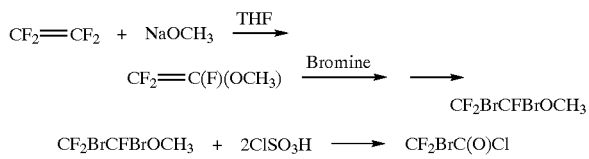

The final yield of $CF_2BrC(O)Cl$ relative to the tetrafluoroethylene $C_2F_4$ is less than 30%.

Difluorohaloacetyl fluorides may also be obtained from $C_2F_4$.

In particular, bromodifluoroacetyl fluoride may be obtained according to the steps described below in the Japanese patent application published under No. JP 82 40434:

$CF_2BrCF_2Br$ (obtained according to $CF_2=CF_2+Br_2$)+ $SO_3$ (or $HSO_3F$) gives an intermediate containing the group $BrCF_2CF_2OSO_2$—.

This intermediate is heated with $H_2SO_4$ or KF/sulfolane and leads to bromodifluoroacetyl fluoride $CF_2BrC(O)F$.

This fluoride may also be obtained by a method described in Japanese patent application JP 57-40433 published on 6 Mar. 1982 which consists in treating $BrCF_2CFClBr$ with an oleum having an $SO_3$ content by weight ranging from 50% to 70% at a temperature of between −10° C. and 120° C., using a molar proportion of $SO_3$ ranging from 0.2 to 5 times the quantity of $BrCF_2CFClBr$ used.

The most cited methods consist nevertheless in carrying out a sulphuric hydrolysis, in the presence of catalysts such as metal salts, in particular mercuric salts, of 1,1-difluorotetrahaloethanes such as $CF_2BrCFClBr$, $CF_2BrCClBr_2$, $CF_2BrCBr_3$, $CF_2BrCF_2Br$.

Thus, PALETA O. et al. (Collect. Czech. Chem. Commun. 35(4) pp. 1302–1306 (1970)) obtained, with a yield of 34%, methyl bromodifluoroacetate by reacting, under reflux for 6 hours, a mixture comprising 60 g of $CF_2BrCFClBr$— 0.217 mol (obtained by bromination of $CF_2=CFCl$), 40 ml of oleum at 60%, that is 0.606 mol of $SO_3$, and 0.5 g of HgO and then introducing the gaseous products formed, containing in particular $CF_2BrC(O)F$ into an ethanolic solution of KF.

The addition of 20 ml of $SO_3$ to the reaction mixture makes it possible to increase the yield of $CF_2BrCO_2CH_3$ to 60.4%.

CAMPBELL R. W. and VOGL O. (Makromol. Chem. 180(3) pp. 633–647 (1979)) obtained methyl bromodifluoroacetate with a yield of 68% using reagents of the same type but with an $SO_3/CF_2BrCFClBr$ molar ratio equal to about 1.6—instead of 2.8 in the method described by PALETA—and a reaction time of 10 hours under reflux. In addition, the oleum used is an oleum at 30%.

MOREL D. and DAWANS (Tetrahedron, 33(12) pp. 1445–1447, (1977)) obtained, with a yield of 85%, ethyl bromodifluoroacetate according to the reaction scheme:

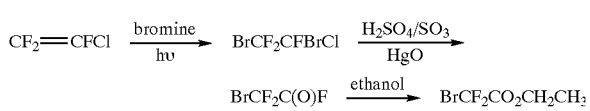

by reacting, at 75° C. for 20 hours, a mixture consisting of 800 g of 1,1,2-trifluoro-1,2-dibromo-2-chloroethane (2.89 mol), a quantity of oleum at 40% so as to have an $SO_3/BrCF_2CFClBr$ molar ratio equal to 1.5 and 7 g of mercuric oxide (HgO).

The bromodifluoroacetyl fluoride ($BrCF_2C(O)F$) which is evolved is trapped in absolute ethyl alcohol.

These authors mention that in the absence of HgO, the conversion of $BrCF_2CFClBr$ is very low.

Patent DE 1020970 describes the preparation of $CF_2BrC(O)Cl$ according to a similar method which consists in treating $CF_2BrCClBr_2$ with an oleum in the presence of $HgSO_4$, for one hour at 45° C. according to the reaction:

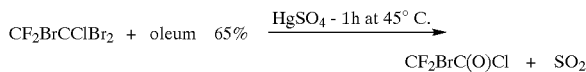

Bromodifluoroacetyl chloride is obtained with a yield of 56%.

It should also be noted that it is possible to obtain bromodifluoroacetyl fluoride (in the form of a mixture with bromodifluoroacetyl bromide) by autooxidation of 1,1-dibromo-2,2-difluoroethylene $CF_2=CBr_2$ which is itself obtained from vinylidene fluoride as described by H. COHN and E. D. BERGMANN in Israel Journal of Chemistry, vol. 2, pp. 355, 361, 1964.

1,1-Dibromo-2,2-difluoroethylene is prepared from vinylidene fluoride by successive bromination and dehydrobromination reactions according to the scheme:

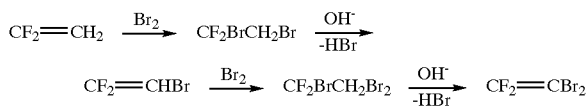

The bromination of vinylidene fluoride is carried out without solvent, under UV irradiation with a quantitative yield. The dehydrobrominations are carried out in aqueous alkaline medium. The overall molar yield of $CF_2=CBr_2$ relative to $CF_2=CH_2$ is 63%.

The autooxidation of $CF_2=CBr_2$ with oxygen leads to a mixture of bromodifluoroacetyl bromide (53%) and dibromofluoroacetyl fluoride (37%) with a yield of the order of 90%. The corresponding ethyl esters are obtained by direct reaction of the mixture of acid halides with ethanol at 0° C.

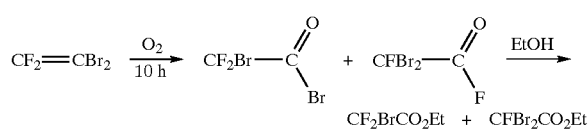

After separation of the esters by distillation, the molar yield of ethyl bromodifluoroacetate relative to dibromodifluoroethylene is then of the order of 25%, hence a yield relative to vinylidene fluoride of less than 16%.

It should be noted-that CHANG-MING HU et al. (Journal of Fluorine Chemistry, 49 (1990) p. 275–280) have described a fairly general method which converts a haloethane to the corresponding acid by reacting stoichiometric quantities of polyfluoroperhaloalkane and a redox pair consisting of ammonium persulphate and sodium formate.

Thus, 1,1,2-trifluoro-2-chloro-1,2-dibromoethane is converted to bromodifluoroacetic acid according to the reaction:

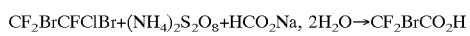

with a yield of 63.4% and a total conversion of $CF_2BrCFClBr$.

The reaction is carried out at 15° C. in DMF medium with bubbling of air. Once the reaction is complete, the medium is poured into water and the strongly acidic solution is extracted with ether. The ether extract is neutralized with an aqueous $NaHCO_3$ solution. The aqueous phase is evaporated to dryness and then the residue ($CF_2BrCO_2Na$) is taken up in concentrated $H_2SO_4$ and then distilled.

GRINDHALL G. A. et al. (J. Org. Chem. 32(3) pp. 603–607 (1967)) obtained ethyl bromodifluoroacetate with a yield of about 50% relative to vinylidene fluoride using the reactions below:

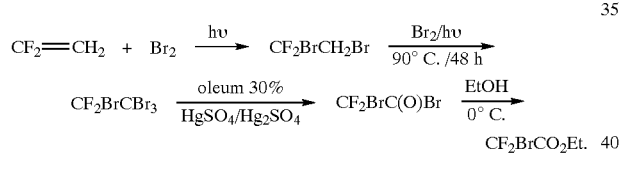

The first step for brominating vinylidene fluoride is carried out at room temperature under UV irradiation with a quantitative yield. Perbromination is more difficult (low productivity) and $CF_2BrCBr_3$ is obtained with a yield of 82.5% relative to $CF_2BrCH_2Br$.

The hydrolysis of $CF_2BrCBr_3$ with oleum 30% uses 6% by weight of mercuric sulphate and 1% by weight of mercurious sulphate. After 12 hours under reflux, the acid bromide $CF_2BrC(O)Br$ is distilled and recovered in ethanol to form ethyl bromodifluoroacetate with a yield of 60.5% relative to $CF_2BrCBr_3$.

Bromodifluoroacetyl fluoride was also obtained by decomposition of $CF_2BrCFClBr$ or of $CF_2BrCF_2Br$ with oleum at 60% in the presence of a catalyst such as $ZnSO_4$, CuO, MnO, ZnO and $Fe_2O_3$ (Japanese patent application JP 11-80084 published on 23 Mar. 1999).

All these methods have numerous disadvantages. Some raw materials used to obtain the bromodifluoroacetyl halides are either difficult to obtain industrially or are dangerous to handle, requiring very specific appliances ($CF_2=CF_2$, $CF_2=CBr_2$).

The use of bromodifluoroacetyl fluoride generates effluents containing hydrofluoric acid or inorganic fluorides requiring the use of special and expensive reactors resistant to HF and to fluorides.

In addition, these methods most often use, in order to increase the yields of hydrolysis of difluorotetrahaloethanes, catalysts which are dangerous for the environment (mercury salts).

The applicant has found that by using reagents which are industrially available or which are easily industrially accessible, it obtained high yields of bromodifluoroacetic compounds, without the need to use toxic catalysts and without producing effluents containing HF or fluorides.

SUMMARY OF THE INVENTION

The subject of the invention is therefore a method for preparing bromodifluoroacetic acid or its esters of formula $CF_2BrCO_2R$ (1) in which R represents a linear or branched, aliphatic hydrocarbon radical having a number of carbon atoms ranging from 1 to 10 and, preferably, ranging from 1 to 8, a benzyl radical, characterized in that it comprises converting a 1,1-difluoro-1,2-dibromodihaloethane of formula $CF_2BrCBrXY$ (2) in which X and Y, which are identical or different, represent a bromine atom or a chlorine atom, to bromodifluoroacetyl halide $CF_2BrC(O)Z$ (3) with Z=Br or Cl, by means of an oleum having an $SO_3$ concentration by weight ranging from 50% to 70%, and then in directly reacting the bromodifluoroacetyl halide (chloride and/or bromide), continuously extracted from the reaction medium, either with an alcohol ROH (4) in order to obtain an alkyl bromodifluoroacetate, or with water in order to obtain bromodifluoroacetic acid.

According to the present invention, the bromodifluoroacetic compounds are obtained from a 1,1-difluoro-1,2-dibromodihaloethane according to two chemical reactions which are carried out without isolating the bromodifluoroacetyl halide according to the reaction schemes:

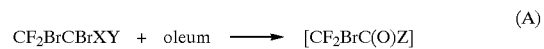 (A)

 (B1)

 (B2)

In a first instance, $CF_2BrCBrXY$ is converted to bromodifluoroacetyl halide by means of an oleum having an $SO_3$ concentration by weight ranging from 50% to 70% so that the $SO_3/CF_2BrCBrXY$ molar ratio is between 1 and 4 and, preferably, between 1 and 2.5. The reaction is carried out at atmospheric pressure and at a temperature such that the bromodifluoroacetyl halide $[CF_2BrC(O)Z]$ is vaporized from the reaction medium in which the reaction (A) is carried out. This reaction temperature is at most equal to 120° C. and is advantageously between 40° C. and 100° C.

To maintain an optimum $SO_3$ concentration in the reaction medium, it is advantageously possible, according to the present invention, to cool the ports leaving the reaction medium so as to cause the $SO_3$ to retrograde.

The reaction product $[CF_2BrC(O)Z]$, which is continuously extracted from the reaction medium, is brought into contact with an alcohol ROH (4) at a temperature at most equal to the reflux temperature of the alcohol ROH used.

As regards the production of bromodifluoroacetic acid, the reaction product $[CF_2BrC(CO)Z]$ continuously extracted from the reaction medium is brought into contact with water.

The alkyl bromodifluoroacetates are then isolated by methods known to persons skilled in the art such as in particular by fractional distillation. Bromodifluoroacetic acid may be extracted using solvents such as esters and then distilled.

According to the present invention, 1,1-difluoro-1,2-dibromodihaloethanes $CF_2BrCBrXY$ in which $X=Y=Br$ or alternatively $X=Y=Cl$ will be preferably used.

Thus, 1,2-dibromo-1,1-difluoro-2,2-dichloroethane $CF_2BrCCl_2Br$ ($X=Y=Cl$) may be easily obtained from 1,1-difluoro-1,2,2-trichloroethane (F 122) according to the reactions:

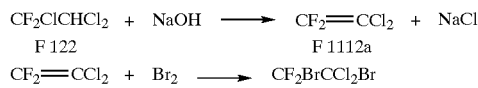

The dehydrochlorination is generally carried out using sodium hydroxide in the presence of a phase transfer agent, at a temperature of between 50° C. and 70° C., with vigorous stirring. The bromination of F1112a is carried out without using a solvent or a catalyst, by simply bubbling in bromine.

1,1-Difluorotetrabromoethane $CF_2BrCBr_3$ ($X=Y=Br$) may be obtained from vinylidene fluoride $CF_2=CH_2$ according to the reactions:

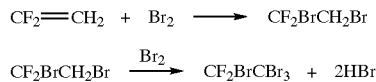

By way of illustration of alcohols ROH which can be used according to the present invention, there may be mentioned methanol, ethanol, isopropanol, n-butanol, 2-ethylhexanol, benzyl alcohol.

The invention applies most particularly to the preparation of ethyl bromodifluoroacetate.

The method which is the subject of the present invention makes it possible to obtain, with high yields, bromodifluoroacetic compounds, alkyl bromodifluoroacetates or bromodifluoroacetic acid without generating effluents containing HF or inorganic fluorides, without using catalysts and from industrially available raw materials.

The examples which follow illustrate the invention.

EXAMPLES

Example 1

Production of Ethyl Bromodifluoroacetate (BDFAE) from 1,2-dibromo-1,1-difluoro-2,2-dichloroethane $CF_2BrCCl_2Br$ a) Preparation of $CF_2BrCCl_2Br$
Reactions:

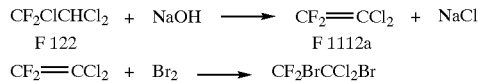

Preparation of 1,1-difluoro-2,2-dichloroethylene (F1112a)

508.5 g (3 mol) of F122 and 2 g of Noramium M2C (dicocodimethylammonium chloride) are loaded into a 1 litre Sovirel-type glass reactor previously dried and inerted with nitrogen, provided with mechanical stirring, an isobaric dropping funnel and a distillation column equipped with a device which makes it possible to adjust the refluxing rate.

The reaction medium is heated to between 50° C. and 70° C., and then 439 g (3.3 mol) of a 10N sodium hydroxide solution are poured in over 3 hours. As the reaction progresses, F1112a distils and is recondensed in a cold dry ice trap.

At the end of the reaction, a 97% conversion of F122 is obtained with an F1112a yield of 94%.

Preparation of 1,2-dibromo-1,1-difluoro-2,2-dichloroethane 678 g (4.24 mol) of bromine are loaded into a 1 litre glass reactor provided with mechanical stirring (anchor), a temperature probe, a return condenser (−8° C.) and a tube for injecting F1112a connected to the storage bottle placed on a balance.

The F1112a previously obtained is then introduced in gaseous form by heating the bottle (40° C.), in liquid bromine at a mean rate of 1 mol/h. The temperature of the reaction medium is maintained between 40° C. and 60° C. so as to maintain the liquid medium without losing too much bromine.

After having introduced 545 g (4.1 mol) of F1112a, the addition is stopped and the stirring maintained for an additional 30 min. The assembly is purged with nitrogen and then an aqueous sodium sulphite solution (10%) is added so as to destroy the excess bromine. The crude product is recovered by decantation and is washed again with water. 1 118 g of product are thus recovered, that is a yield of 93%.

b) Production of Ethyl Bromodifluoroacetate $CF_2BrCO_2CH_2CH_3$ (BDFAE) according to the invention:

Reaction scheme:

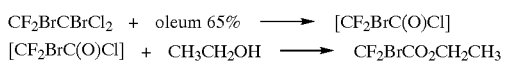

Procedure:

153 g (0.5 mol) of 1,2-dibromo-1,1-difluoro-2,2-dichloroethane obtained above are loaded into a first glass reactor of 500 cm³, provided with mechanical stirring, an isobaric dropping funnel and a distillation column surmounted with a timer for adjusting the refluxing rate.

The draw-off of the column is connected to a second reactor containing 92 g of ethanol. This reactor is cooled by means of a jacket (−5° C.) and is provided with mechanical stirring and a condenser connected to a water absorber.

The reagent in the first reactor is heated to 50° C., and then 123 g of oleum 65% are poured in over 2 h 30 min, which corresponds to 1 mol of $SO_3$. The distilling fraction drawn off continuously, which contains bromodifluoroacetyl halide, is esterified in the second reactor whose temperature is maintained at around 25° C. At the end of the reaction, the apparatus is flushed with nitrogen and cooled to room temperature.

The content of the second reactor is washed with a 7% sodium sulphite solution. The organic phase is recovered by decantation. The ethyl bromodifluoroacetate yield relative to the perhalogenated derivative is 82%. BDFAE is purified by distillation under reduced pressure.

Ethyl bromodifluoroacetate was identified by proton, carbon 13 and fluorine 19 nuclear magnetic resonance (NMR) on a multinucleus AC300 type Brücker apparatus (frequencies for $^1H=300$, 13 MHz, for $^{13}C=75.47$ MHz and for $^{19}F=282.4$ MHz). NMR identification of $CF_2BrC(O)OCH_2CH_3$ a b c d $^{13}C$ NMR spectrum:
(solvent=$CDCl_3$)
$\delta a=108.8$ ppm δb=159.5 ppm
δc=64.5 ppm
δd=13.5 ppm
$^{19}$F NMR spectrum:
(solvent=CDCl$_3$/external standard: trifluoroacetic acid)
δ (CF$_2$Br)=16.8 ppm
coupling constant $J^1_{C-F}$=314 Hz
coupling constant $J^2_{C-F}$=31 Hz
$^1$H NMR spectrum:
(solvent=CDCl$_3$/internal standard: tetramethylsilane)
δ (C$\underline{H}_2$)=4.42 ppm
δ(C$\underline{H}_3$)=1.40 ppm Example 2

Production of Bromodifluoroacetic Acid from CF$_2$BrCCl$_2$Br 153 g (0.5 mol) of 1,2-dibromo-1,1-difluoro-2,2-dichloroethane obtained above are loaded into a first glass reactor of 500 cm$^3$, provided with mechanical stirring, an isobaric dropping funnel and a distillation column surmounted with a timer for adjusting the refluxing rate.

The draw-off of the column is connected to a second reactor containing 150 g of water. This reactor is cooled by means of a jacket (5° C.) and is provided with mechanical stirring and a condenser connected to a water absorber.

The reagent in the first reactor is heated to 50° C., and then 123 g of oleum 65% are poured in over 2 h 30 min, which corresponds to 1 mol of SO$_3$. The distilling fraction drawn off continuously, which contains bromodifluoroacetyl halide, is hydrolysed in the second reactor whose temperature is maintained at around 25° C. At the end of the reaction, the apparatus is flushed with nitrogen and cooled to room temperature.

A 7% sodium sulphite solution is added to the content of the second reactor so as to destroy the traces of bromine. The bromodifluoroacetic acid is then extracted with isopropyl ether and then distilled under reduced pressure. The yield of bromodifluoroacetic acid relative to the perhalogenated derivative is 80%.

Example 3

Production of Ethyl Bromodifluoroacetate (BDFAE) from 1,1-difluorotetrabromoethane CF$_2$BrCBr$_3$
a) Preparation of CF$_2$BrCBr$_3$ by Thermal Bromination of 1,1-difluoro-1,2-dibromoethane CF$_2$BrCH$_2$Br:

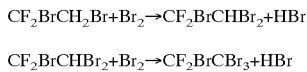

The bromination is carried out in gas phase in a quartz tube (having a diameter of 2.2 cm and a length of 39 cm) placed vertically and heated by means of an electric oven. 0.12 mol/h of CF$_2$BrCH$_2$Br and 0.30 mol/h of bromine are simultaneously continuously introduced at the top of the tube. After a residence time of 20 seconds in the tube at a temperature of 520° C., the vapours leaving at the bottom of the tube are condensed through a double circulation condenser (at −10° C.) and the condensate is collected in a glass receptacle. The ports of the receptacle are connected to a water washer in order to absorb the hydrobromic acid formed, followed by a dry ice trap in order to recover the potential volatile organics.

After continuously working for 6 h, the crude product of bromination collected in the receptacle is concentrated in a rotary evaporator in order to remove the excess bromine. 225.5 g of an organic oil are thus recovered which contain 3.3% of CF$_2$BrCH$_2$Br, 24.8% of CF$_2$BrCHBr$_2$ and 67.5% of CF$_2$BrCBr$_3$ (composition by weight determined by vapour phase chromatography). The crude molar yield of CF$_2$BrCBr$_3$ relative to 1,1-difluoro-1,2-dibromoethane used is thus 55.3%.

After topping by fractional distillation under reduced pressure, 79.5 g of distillate comprising about 9% of unconverted CF$_2$BrCH$_2$Br, 70% of intermediate product of bromination CF$_2$BrCHBr$_2$ and 18% of CF$_2$BrCBr$_3$ are recovered and 141.5 g of 1,1-difluorotetrabromoethane having a purity greater than 97%, which can be directly used for subsequent synthesis of BDFAE, remain in the distiller.

The distillate being recyclable to the bromination stage, the true yield of manufacture of 1,1-difluorotetrabromoethane relative to the 1,1-difluoro-1,2-dibromoethane consumed is of the order of 83%. b) Synthesis of BDFAE:

The synthesis is carried out in the same apparatus and according to the same methodology as in Example 1 (b).

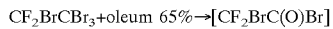

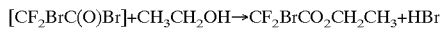

118 g (0.3 mol) of 1,1-difluorotetrabromoethane obtained above are loaded into the first reactor and heated to 100° C. 86.1 g of oleum 65% (corresponding to 0.7 mol of SO$_3$) are then poured in over 1 h 30 min.

The bromodifluoroacetyl bromide contained in the continuously extracted distillate is esterified in the second reactor containing 100 g of ethanol maintained at a temperature of the order of 30° C. At the end of the reaction, the ethanolic phase is stripped with nitrogen and washed with a sodium sulphite solution. The ethanolic phase recovered after decantation is concentrated in a rotary evaporator and then the BDFAE is extracted from the residual organic raw material and purified by distillation under reduced pressure. 48.2 g of BDFAE are thus obtained with a purity greater than 98% corresponding to a net molar yield of 77.5% relative to the initial 1,1-difluorotetrabromoethane.

The preceding examples can be repeated with similar success by substituting the generically or specifically described reactants and/or operating conditions of this invention for those used in the preceding examples.

The entire disclosure of all applications, patents and publications, cited above and below, and of corresponding French Application No. 01/07943, filed Jun. 18, 2001 is hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:
1. A method for preparing compounds of the formula CF$_2$BrCO$_2$R in which R represents a hydrogen atom, a linear or branched, aliphatic hydrocarbon radical having 1 to 10 carbon atoms or a benzyl radical, said method comprising, in the absence of a catalyst, converting a 1,1-difluoro-1,2-dibromodihaloethane of formula CF$_2$BrCBrXY in which X and Y, which are identical or different, represent a bromine atom or a chlorine atom, to bromodifluoroacetyl halide CF$_2$BrC(O)Z with Z=Br or Cl, with an oleum having an SO$_3$ concentration by weight ranging from 50% to 70%, continuously extracting the bromodifluoroacetyl halide from the reaction medium, and directly reacting the bromodifluoro- acetyl halide continuously extracted from the reaction medium, either with an alcohol ROH, or with water.

2. A method according to claim 1, wherein the 1,1-difluoro-1,2-dibromodihaloethanes of formula $CF_2BrCBrXY$ are compounds of formula:

$CF_2BrCCl_2Br$ and $CF_2BrCBr_3$.

3. A method according to claim 1, wherein the alcohol ROH is ethanol.

4. A method according to claim 1, wherein the oleum has an $SO_3$ concentration by weight equal to 65%.

5. A method according to claim 1, wherein the $SO_3/CF_2BrCBrXY$ molar ratio is between 1 and 4.

6. A method according to claim 1, wherein the conversion of $CF_2BrCBrXY$ to $CF_2BrC(O)Z$ is carried out at a temperature such that the bromodifluoroacetyl halide is vaporized from the reaction medium in which the conversion is carried out.

7. A method according to claim 6, wherein the temperature for converting $CF_2BrCBrXY$ to $CF_2BrC(O)Z$ :s at most equal to 120° C.

8. A method according to claim 1, wherein the bromodifluoroacetyl halide $CF_2BrC(O)Z$ is reacted with the alcohol ROH at a temperature at most equal to the reflux temperature of the alcohol ROH.

9. A method according to claim 1, for preparing ethyl bromodifluoroacetate.

10. A method according to claim 1, wherein R is an aliphatic hydrocarbon of 1–8 carbon atoms.

11. A method according to claim 5, wherein the $SO_3/CF_2BrCBrXY$ molar ratio is between 1 and 2.5.

12. A method according to claim 5, wherein the temperature for converting $CF_2BrCBrXY$ to $CF_2BrC(OZ$ is at most equal to 120° C.

13. A method according to claim 6, wherein the temperature for converting $CF_2BrCBrXY$ to $CF_2BrC(O)Z$ is between 40° C. and 100° C.

14. A method according to claim 5, wherein the temperature for converting $CF_2BrCBrXY$ to $CF_2BrC(O)Z$ is between 40° C. and 100° C.

15. A method according to claim 11, wherein the temperature for converting $CF_2BrCBrXY$ to $CF_2BrC(O)Z$ is between 40° C. and 100° C.

16. A method according to claim 1, wherein said continuously extracting comprises withdrawing vapors of bromodifluoroacetyl halide from the reaction medium.

17. A method according to claim 1, wherein at least one of X and Y is Cl.

18. A method according to claim 1, wherein both X and Y represent Cl.

* * * * *